United States Patent [19]

Corin et al.

[11] Patent Number: 4,994,192
[45] Date of Patent: Feb. 19, 1991

[54] AMINE POLYMERS AS COAGULATOR ACCELERATORS IN BLOOD PHASE SEPARATION

[75] Inventors: Alan F. Corin; Richard L. Columbus; Deborah P. Freyler, all of Rochester, N.Y.

[73] Assignee: Eastman Kodak Company, Rochester, N.Y.

[21] Appl. No.: 465,835

[22] Filed: Jan. 16, 1990

[51] Int. Cl.$^5$ ............................................. B01D 21/26
[52] U.S. Cl. .................................... 210/782; 210/789; 210/516
[58] Field of Search ............... 210/781, 782, 789, 359, 210/360.1, 513-516, 518, 927

[56] References Cited

U.S. PATENT DOCUMENTS 3,902,964  9/1975  Greenspan .............................. 195/1
4,050,451  9/1977  Columbus ............................ 128/2 F
4,478,944  10/1984  Gross et al. ........................... 436/95

FOREIGN PATENT DOCUMENTS 129790  10/1979  Japan .
58-49410  3/1983  Japan .
2785885  2/1985  Japan .

Primary Examiner—Frank Sever
Attorney, Agent, or Firm—Dana M. Schmidt

[57] ABSTRACT

Apparatus and a method are described, wherein a coagulator accelerator is added to a container to achieve agglutination of blood cells when centrifuging whole blood, allowing the serum to be more easily poured off. The accelerator is selected from polymeric amines that are either polymerized amino acids or vinyl addition polymer amines, with a specified molecular weight range, the vinyl addition amines being selected to avoid lysing the blood cells.

10 Claims, No Drawings

AMINE POLYMERS AS COAGULATOR ACCELERATORS IN BLOOD PHASE SEPARATION

FIELD OF THE INVENTION

This invention relates to apparatus and a method for agglutinating blood cells during centrifuging to allow separation of the serum.

BACKGROUND OF THE INVENTION

In the blood-testing field, assays of interest frequently are limited to tests applied to serum or plasma, rather than to whole blood. The reason is that the cell fraction of whole blood has constituents that may interfere with or obscure the assay. For such assays, a preliminary step is phase separation, in which the cellular fraction is separated and removed.

Whatever the mode of separation that is used, and centrifugation is one of the most common, some means is usually employed to maintain the phase separation after it is achieved, to permit physical separation of the phases without resuspension. One of the most common is the use of a gel having a specific gravity between that of the two phases, as is illustrated by U.S. Pat. No. 4,050,451. Although such a gel is often adequate, it does have weaknesses. One is that it provides only a mechanical barrier, and such barriers can fail. For example, severe agitation of the container in which the gel barrier is in place, can produce failure.

Therefore, prior to the invention there has been a need for a substance to maintain phase separation, that is not simply a breachable wall between the two phases. More specifically, there has been a need for such a substance that provides a substantially irreversible phase separation even in the face of substantial agitation.

Polymeric "coagulants" have been known heretofore, for example, those described in Japanese Kokai No. 58/49410. However, the substances specifically described are for sewage separation, and are polymers in which the pendant amines are fully substituted to create quaternary amines. Blood requires much greater care in handling than sewage so that what works in sewage will not necessarily work in blood. For example, it is important that the polymer not cause lysing of the blood cells. Furthermore, the charge of the polymer must be adequate to effect maintenance of phase separation, without being so strong as to set up a charge gradient causing ion leakage through the membranes of the blood cells. As an example of how polymers can be satisfactory for sewage separation but not for blood separation, it will be shown hereinafter that some polymers with quaternary amines do not work satisfactorily.

On the other hand, U.S. Pat. No. 3,902,964 describes coagulator accelerators that are used strictly with whole blood to coagulate blood cells in an accelerated manner. However, two such agents are required—Polybrene and a lectin. Furthermore, Polybrene is hexadimethrine bromide, a polymeric structure that does not lend itself to significant structural modification to provide workable alternatives. In contrast, vinyl addition polymers are much more versatile. However, as will become apparent, not any vinyl addition polymer is effective.

There has been a need, therefore, prior to this invention, to identify a class of coagulator accelerators capable of variation, and which will cause permanent coagulation of blood cells during centrifuging, without lysing and without requiring other accelerators as well.

SUMMARY OF THE INVENTION

We have discovered an improved class of blood coagulator accelerators that provide remarkable stability against resuspension of the separated phases, even without using any other coagulator besides those of this class.

More particularly in accord with one aspect of the invention, there is provided apparatus for separating and maintaining separated in a centrifuge, red cells from other constituents of whole blood, comprising a compartment constructed to receive whole blood for phase separation, and within the compartment, an effective amount of a coagulator accelerator agent for preventing the red cells from becoming resuspended when the compartment's contents are agitated. The agent is (a) effective without other coagulator accelerators, (b) positively charged at neutral pH, and (c) selected from a polymer that is either a polymerized amino acid having a weight average molecular weight ($\overline{M}w$) of between about 35 k and about 500 k Daltons, determined by the LALLS light scattering technique, or a vinyl addition amine polymer having a polyvinyl pyridine equivalent weight average molecular weight (PVP-eq. $\overline{M}w$) of between about 40 PVP-eq. k Daltons and 6000 PVP-eq. k Daltons wherein the amine is a primary, secondary, tertiary or quaternary amine pendant from the polymer backbone and having a structure that is effective to coagulate without causing lysing of red blood cells.

In accord with another aspect of the invention, there is provided a method of coagulating blood cells while centrifuging whole blood to separate out the serum, the method comprising the steps of (a) admixing in a container, a sample of whole blood and as a coagulator accelerator, an effective amount of an agent that is positively charged at neutral pH and is a polymer that (i) is in the form of either a polymerized amino acid having a weight average molecular weight of between about 35 k and about 500 k Daltons determined by the LALLS light scattering technique, or a vinyl addition amine polymer having a $\overline{M}w$ of between about 40 PVP-eq. k Daltons and about 6000 PVP-eq. k Daltons wherein the amine is a primary, secondary, tertiary or quaternary amine pendant from the polymer backbone and having a structure that is effective to coagulate without causing lysing of red blood cells, the agent being effective without other coagulator accelerators present, and (b) spinning the container about a centrifuge axis at a speed sufficient to cause phase separation of the serum and blood cells, the quantity of acceleration being sufficient to cause the cells to permanently coagulate without lysing.

In accord with yet another aspect of the invention, there is provided, as a result of the above-described apparatus and method, a coagulated blood sample comprising serum, and adjacent thereto agglutinated blood cells intermixed with an effective amount of a coagulator accelerator agent for preventing the red cells from becoming resuspended when the compartment's contents are agitated, the agent being (a) effective without other coagulator accelerators, (b) positively charged at neutral pH, and (c) selected from a polymer that is either a polymerized amino acid having a weight average molecular weight ($\overline{M}w$) of between about 35 k and about 500 k Daltons, determined by the LALLS technique, or a vinyl addition amine polymer having a PVP-eq. $\overline{M}w$ of between about 40 PVP-eq. k Daltons and 6000 PVP-eq. k Daltons wherein the amine is a primary, secondary, tertiary or quaternary amine pendant from the polymer backbone and having a structure that is effective to coagulate without causing lysing of red blood cells.

Therefore, it is an advantageous feature of the invention that substantial stability in blood phase separation, that resists resuspension even in the face of inversion, can be achieved without the risk of hemolysis.

It is another advantageous feature of the invention that such stability is achieved using a class of coagulator accelerators that permits substantial structural variation, and yet is effective without the addition of any other agent to achieve the purpose.

Other advantageous features will become apparent upon reference to the following Description of the Preferred Embodiments.

DESCRIPTION OF THE PREFERRED EMBODIMENTS

The advantageous features of the invention are achieved by the discovery of a class of polymers having a charged nitrogen positioned in such a way that the charge is effective to agglutinate the cells but ineffective to cause lysing of the cells. The exact mechanism and underlying essential polymeric structure by which this is achieved is not well understood. The class of useful materials has been empirically determined, by a test hereinafter set forth.

The coagulator accelerator of this invention is a polymeric amine or polymerized amino acid, and as such is most often and most conveniently obtained as an acid addition salt. In addition, the free amine form is believed to be useful. Thus, the coagulator accelerator can be:

(A) any vinyl addition polymer having the requisite pendant amine groups and PVP-eq. $\overline{M}w$, or (B) the residue of a polymerized amino acid having the requisite $\overline{M}w$. Such polymerized residues have weight average molecular weights measured by the "low angle laser light scattering" technique, herein abbreviated LALLS. The LALLS technique is conventional, and is described, e.g., in *Steric Exclusion Liquid Chromatography of Polymers*, ed. by J. Janca (1984), especially pages 227-233.

Because of the effectiveness of this accelerator, it is most preferably used as the sole coagulator accelerator, to save on the expense of using a second agent in combination. However, several of the agents of this class can be used together.

A preferred class of polymeric amines are vinyl addition polymers having recurring units with the structural formula:

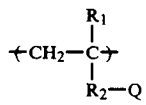
(I)

wherein $R_1$ is H or alkyl of 1-3 carbon atoms; $R_2$ is phenylenemethylene —$CO_2R_3$— or

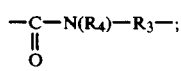

$R_3$ is alkylene of 1 to 6 carbon atoms, for example, methylene, ethylene, propylene and the like; $R_4$ is alkyl of 1 to 4 carbon atoms or H; Q is a primary, secondary, tertiary or quaternary amine that does not lyse blood cells. The number of repeating units is that needed to create a PVP-eq. $\overline{M}w$ of between about 40 PVP-eq. k Daltons and about 6000 PVP-eq. k Daltons.

Of the substituted amines comprising Q in formula (I) above, most preferred are those having the formula

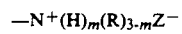

wherein m is 1, 2 or 3; Z is an acid anion, and R is selected from the group consisting of alkyl or cycloalkyl of 1 to 8 carbon atoms, for example, methyl, ethyl, propyl, iso-propyl, benzyl and the like; and cyclohexyl, i.e.,

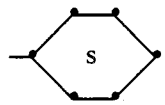

The most preferred polymers of formula (I) have the amine joined to an alkylene that is preferably —(CH$_2$)$_2$— or —(CH$_2$)$_3$—, and m is 1 or 3.

In the case in which the polymeric coagulator accelerator bears an uncharged amine as supplied, for example, a primary amine, it is believed that these become the acid salt when added to whole blood.

In the vinyl addition polymer amines, most preferred are those that are free of long-chain oleophilic substituents on the amine nitrogen.

Alternatively, the polymer can be the residue of a polymerized amino acid, and in such a case, any polymeric amino acid can form the residue, if it will protonate at a neutral pH. The best results are obtained by amino acids having a side chain pKa of at least 9.0. Although the examples hereinafter described feature polylysine, polymers of other naturally occurring amino acids are also considered to be useful. Such polymers can form the recurring unit $$+NH-\overset{H}{\underset{R_5}{C}}-\overset{O}{\overset{\|}{C}}+$$ (II)

$R_5$ provides the pendant amine group. It is also $R_5$ that gives the variability that distinguishes between the amino acids. For example, $R_5$ can be from the following amino acids:

| $R_5$ | Amino Acid |
|---|---|
| —(CH$_2$)$_3$NH$_2$ | ornithine |
| —(CH$_2$)$_4$NH$_2$ | lysine |
|  | arginine |

All the above polymerize through the amine and the acid group.

Regardless of the amino acid selected for the polymerization, molecular weight is critical. If the molecular weight is too small or too large, the maintenance of phase separation is lost. It has been found that the preferred values are between about 75 k Daltons and about 300 k Daltons, as determined by the LALLS light scattering technique. Just which value is most preferred within this range depends upon the amino acid that is selected.

Test

To determine whether a given polymer will be satisfactory, by itself, as a blood coagulator accelerator for purpose of this invention, the following procedure was used, and is to be used for this invention:

Varying amounts of the polymer in question were added, for each example testing a specific amount, to 1 mL of whole blood poured out of 7 mL vacutainer tubes used for collection and containing ethylenediaminetetraacetic acid (EDTA) as a conventional anticoagulant. The mixture was centrifuged for 5 min. in an appropriate stoppered container. Any stoppered container is useful for this test or the invention, of the appropriate volume. The centrifuge was either a Kubota Hematocrit KH-1200M model with a 9 cm. spin radius, spun at about 1610 g's, or a vertical centrifuge similar to that described in U.S. Pat. No. 4,675,001, having a 2.54 cm spin radius and spun at about 453 g's. The effect of the candidate coagulator polymer was judged qualitatively. Successful agglutination was assessed visually by observing the formation of an interface between red cells and clear plasma. Interface stability could be ascertained by oscillation of the sample in a direction perpendicular to the plane of the interface, and by complete inversion of the container to see if the agglutination clump will float through the serum without breaking off sub-clumps of cells. The results were scored as follows:

0—no agglutination of the cells was seen.
1—subclumps broke off even when only oscillating the sample in a direction perpendicular to the plane of the interface.
2—no subclump breakage occurred until the container was inverted and then some breakage occurred.
3—the clump stayed together even when the container was inverted.

It will be readily apparent that complete resistance to resuspension, as determined by container inversion (a "3"), is preferred over the "1" or "2" results showing resistance to resuspension during oscillation. However, even the "slight" agglutination of "1" or "2" is acceptable and an improvement over no agglutination if care is taken to not invert the container before or during "pour-off" of the serum phase.

Hemolysis, a property that must be avoided, was detected by observing the serum phase that resulted. Any red color is indicative, of course, of hemolysis occurring. However, in some cases only a slight cloudiness is observed, which is believed to be some proteinaceous contamination short of actual hemolysis. Such cloudiness is believed to be acceptable, provided that the user be sure NOT to test such serum sample for total protein or the like.

In use, the resulting separated serum is poured off from the coagulated blood cells, and tested for the analyte of choice. Except as noted hereinafter, any analyte test is appropriate, for example: albumin, alkaline phosphatase, amylase, aspartate amino transferase, blood urea nitrogen, calcium, chloride, cholesterol, creatin kinase (MB), creatinine, gamma glutamyltransferase, glucose, hemoglobin, lactate dehydrogenase, magnesium, phosphorous, potassium, sodium, total bilirubin, total protein and uric acid. However, interference was observed using poly(2-aminoethyl methacrylate hydrochloride) to separate serum that was then tested for the following blood analytes: alanine, aminotransferase, ammonia, carbon dioxide, high density lipoprotein cholesterol, lipase, theophylline and triglyceride.

Preferred Coagulator Accelerators

The following are the preferred members of the useful class of materials set forth above, because they produced complete agglutination at at least one concentration, when tested using the inversion of the container. Both homopolymers and copolymers are represented:

| Name | Repeating Unit | Most Preferred Concentration (mg/mL) |
|---|---|---|
| Polylysine | $-(C(H)(-(CH_2)_4-NH_2)-C(=O)-NH)-$ * | 1.65 to 5 |
| poly(2-aminoethyl methacrylate hydrochloride) | $-(CH_2-C(CH_3)(C(=O)-O-(CH_2)_2-NH_2 \cdot HCl))-$ | 0.9 to 1.5 |
| poly[N-(3-aminopropyl methacrylamide)] | $-(CH_2-C(CH_3)(C(=O)-NH-(CH_2)_3NH_2))-$ | 1.5 to 2.0 |

-continued

| Name | Repeating Unit | Most Preferred Concentration (mg/mL) |
|---|---|---|
| poly[N-(3-N, N-dimethyl- aminopropyl) methacrylamide] | $\mathrm{-(CH_2-C(CH_3)-)-\ ;\ C=O;\ NH;\ (CH_2)_3;\ N(CH_3)_2}$ | 1 to 10 |
| poly[2-(N-methylamino)ethyl methacrylate hydrochloride] | $\mathrm{-(CH_2-C(CH_3)-)-\ ;\ C=O;\ O;\ (CH_2)_2;\ H-N-CH_3\cdot HCl}$ | 2.0 to 2.8 |
| poly[acrylamide-co-N-(3-aminopro-pyl)methacryla-mide hydrochloride] (Weight Ratio 20/80) | $\mathrm{-(CH_2-CH(CONH_2))-(CH_2-C(CH_3)(CONH(CH_2)_3NH_2\cdot HCl))-}$ | 0.5 to 2.0 |
| poly(acrylamide-co-2-aminoethyl methacrylate hydrochloride) (Weight ratio 50/50) | $\mathrm{-(CH_2-CH(CONH_2))-(CH_2C(CH_3)(COOCH_2CH_2NH_2\cdot HCl))-}$ | 4.5 to 8.0 |
| poly(N-cyclohexyl-N,N-dimethyl-N-vinylbenzyl-ammonium chloride) | $\mathrm{-(CH_2-CH(C_6H_4-CH_2-N^+(CH_3)_2(C_6H_{11}))Cl^-)-}$ | 2.4 to 8 |

*The structure shown may not be complete in that the pendant primary amine may also undergo polymerization, e.g., to form a branched polymer.

(Of those on the above list, it should be noted that polylysine achieves a complete (or "3") agglutination only if the whole blood is first diluted by a four-fold dilution using isotonic saline.)

The useful range of weight average molecular weights for the polymerized amino acids appears to be from about 35 k Daltons to about 500 k Daltons, measured by the LALLS light scattering technique. This was determined by testing a variety of different molecular weights for polylysine in the above-described "test". The ones that passed the test had $\overline{M}w$ values of 39,000 Daltons, 77,000 Daltons; 143,700 Daltons; 201,000 Daltons; and 410,200 Daltons.

The molecular weight aspects of the vinyl addition polymers is discussed hereinafter under "Preparation".

Not all vinyl addition polymeric amines, or even other forms of polymeric amines, will produce at least a "1" agglutination, as defined above, without hemolysis. Those that failed are set forth hereinafter as Comparative Examples. The distinction does NOT appear to hinge on whether or not the amine is primary, secondary, tertiary or quaternary. A polymeric amine that did succeed (produced a "1" agglutination), but which is not part of this invention since it is not a poly(aminoacid) nor a vinyl addition polymer, is Polybrene.

Preparation

All of the polymeric coagulator accelerators of this invention can be prepared by conventional processes. Illustrated by way of example is poly(2-aminoethyl methacrylate hydrochloride). Forty grams of 2-aminoethyl methacrylate hydrochloride was dissolved in 40 mL of ethanol and 400 ml of distilled water in a one liter round bottom three-neck flask equipped with a nitrogen inlet tube, condenser and stirrer. The solution was nitrogen sparged for 10 minutes and heated to 60° C. by immersion in a constant temperature bath. Then 0.8 grams of azobis(cyanovaleric acid) was added and the reaction allowed to continue for 16 hours with stirring under a nitrogen blanket. The percent solids of the resultant suspension was 9.74%. The pH was raised to 7 from 2.3 with 5% aqueous NaOH and the resultant polymer dialyzed for two days against distilled water by the method of dynamic dialysis. The final yield was determined as 2,115 grams of a 1.39% polymer solution at pH 6.8. Characterization of this polymer proceeded as follows: The refractive index increment of the polymer was obtained versus dialysate after exhaustive dialysis against 0.1N aqueous NaCl through a 1000 molecular weight cut-off membrane. Weight average molecular weights ($\overline{M}w$) were determined by low-angle laser light-scattering (LALLS) in 0.1N NaCl. Poly(2-vinylpyridine) (PVP) equivalent molecular weights were determined by size-exclusion chromatography. Size-exclusion chromatography was run at a flow rate of 0.5 mL/minute in aqueous 0.1M tetraethylammonium nitrate adjusted to pH 2.0 with trifluoroacetic acid. Three columns 4.6 mm×250 mm purchased from Synchrom, Inc. prepacked with CATSEC (trade name) size-exclusion chromatography beads were coupled in series. The pore diameters of the beads in each column were 10, 100, and 1000 nm, respectively.

The poly(2-vinylpyridine) (PVP)-equivalent molecular weight distribution was quite broad and centered about 250,000. This batch of polymer was further fractionated into six fractions as noted below, and the PVP-equivalent molecular weight of each fraction was determined by size-exclusion chromatography as described above. Each of these fractions was tested in the above-noted "Test" procedure, and found to perform satisfactorally:

| PVP-eq. $\overline{M}w$ (Daltons) | Fractions Tested Wt. in Fraction (mg) | PVP-eq. $\overline{M}w$/PVP-eq. $\overline{M}n$ (Dispersion) |
| --- | --- | --- |
| 5,310,000 | 13.6 | 2.42 |
| 2,430,000 | 53.1 | 2.21 |
| 857,000 | 61.9 | 2.13 |
| 328,000 | 19.1 | 2.01 |
| 124,000 | 8.2 | 2.59 |

In addition, 2 mg was found to have a PVP-eq. $\overline{M}w$ below 124,000, but this was an insufficient amount to test.

From this molecular weight study, it was concluded that, within the noted range of PVP-eq. $\overline{M}w$ of 40 PVP-eq. k Daltons to 6000 PVP-eq. k Daltons, the use of vinyl addition polymers in the invention is generally insensitive to the molecular weight of the polymer.

EXAMPLES

The following examples further illustrate the scope of the invention. They were tested by the test procedure set forth above under "Test":

EXAMPLES 1-7

Polylysine Polymers

The primary amine polymers tested were those of Table I. Concentrations were determined as per 1 mL of whole blood. "Comp. Ex." were comparative examples.

TABLE I

| Ex. | Polymer | $\overline{M}w$ (Daltons) | Concentration (mg/mL) |
| --- | --- | --- | --- |
| 1 | polylysine | 39,000 | 0.234 |
| 2 | polylysine | 77,000 | 0.485 |
| 3 | polylysine | 143,700 | 1.0 |
| 4 | polylysine | 201,000 | 1.65 |
| 5 | polylysine | 410,200 | 2.71 |
| 6 | polylysine | 201,000 | 3.3 |
| 7 | polylysine | 201,000 | 5.0 |
| Comp. Ex. 1 | polylysine | 9,900 | 0.079 |
| Comp. Ex. 2 | polylysine | 201,000 | 0.45 |
| Comp. Ex. 3 | polylysine | 201,000 | 1.00 |
| Comp. Ex. 4 | polylysine | 201,000 | 1.15 |
| Comp. Ex. 5 | polylysine | 201,000 | 1.43 |

The results of tests of the primary amine polymers appear in Table II.

TABLE II

| Example | Degree of Agglutination | Serum Integrity |
| --- | --- | --- |
| 1 | 1 | Clear |
| 2 | 3 | Clear |
| 3 | 3 | Clear |
| 4 | 3 | Clear |
| 5 | 1 | Clear |
| 6 | 3 | Clear |
| 7 | 3 | Clear |
| Comp. Ex. 1 | 0 | Clear |
| Comp. Ex. 2 | 0 | Clear |
| Comp. Ex. 3 | 0 | Clear |
| Comp. Ex. 4 | 0 | Clear |
| Comp. Ex. 5 | 0 | Clear |

EXAMPLES 8-39

Other Primary Amine Polymers

The primary amine polymers that were tested are listed in Table III. Only the polymers of Examples 8-11 and Comp. Example 6 had a $\overline{M}w$ determination made, and it was 250,000 as PVP equivalents, in each case. The results of the test are also listed in Table III, the test procedure being identical to that of Example 1.

TABLE III

| Ex. | Polymer | Concentrations (mg/mL) | Degree of Agglut. | Serum Integrity |
| --- | --- | --- | --- | --- |
| 8 | poly(2-aminoethyl methacrylate hydrochloride) | 0.92 | 3 | Clear |
| 9 | poly(2-aminoethyl methacrylate hydrochloride) | 1.38 | 3 | Clear |
| 10 | poly(2-aminoethyl methacrylate hydrochloride) | 1.84 | 1 | Clear |
| 11 | poly(2-aminoethyl | 2.30 | 1 | Clear |

TABLE III-continued

| Ex. | Polymer | Concentrations (mg/mL) | Degree of Agglut. | Serum Integrity |
|---|---|---|---|---|
| | methacrylate hydrochloride) | | | |
| Comp. Ex. 6 | poly(2-aminoethyl methacrylate hydrochloride) | 0.46 | 0 | Clear |
| Comp. Ex. 7 | poly(2-aminoethyl methacrylate hydrochloride-co-2-hydroxyethyl methacrylate) (Weight ratio 20/80) | 0.78 | 0 | Clear |
| Comp. Ex. 8 | poly(2-aminoethyl methacrylate hydrochloride-co-2-hydroxyethyl methacrylate) (Weight ratio 20/80) | 2.34 | 0 | Clear |
| Comp. Ex. 9 | poly(2-aminoethyl methacrylate hydrochloride-co-2-hydroxyethyl methacrylate) (Weight ratio 20/80) | 3.9 | 0 | Clear |
| (Comp. Ex. 7-9 are considered to be in effect alternative concentrations of Ex. 8-11, since it is believed that the alcohol co-monomer of Comp. Ex. 7-9 contributes little to the effect). | | | | |
| 12 | poly[N-(3-aminopropyl)methacrylamide] | 1.65 | 2 | Clear |
| 13 | poly[N-(3-aminopropyl)methacrylamide] | 2.00 | 2 | Clear |
| 14 | poly[N-(3-aminopropyl)methacrylamide] | 3.00 | 2 | Clear |
| Comp. Ex. 10 | poly[N-(3-aminopropyl)methacrylamide] | 1.00 | 0 | Clear |
| 15 | poly[acrylamide-co-N-(3-aminopropyl)methacrylamide hydrochloride] (Weight ratio 20/80) | 0.62 | 3 | Clear |
| 16 | poly[acrylamide-co-N-(3-aminopropyl)methacrylamide hydrochloride] (Weight ratio 20/80) | 1.86 | 3 | Clear |
| 17 | poly[acrylamide-co-N-(3-aminopropyl)methacrylamide hydrochloride] (Weight ratio 20/80) | 3.1 | 1 | Clear |
| 18 | poly[N-3-aminopropyl)methacrylamide-co-2-hydroxyethyl methacrylate (Weight ratio 30/70) | 0.96 | 1 | Clear |
| 19 | poly[N-3-aminopropyl)methacrylamide-co-2-hydroxyethyl methacrylate (Weight ratio 30/70) | 2.88 | 1 | Clear |
| 20 | poly[N-3-aminopropyl(methacrylamide-co-2-hydroxyethyl methacrylate (Weight ratio 30/70) | 4.8 | 1 | Clear |
| 21 | poly[acrylamide-co-2-aminoethyl methacrylate hydrochloride (Weight ratio 50/50)* | 0.95 | 1 | Clear |
| 22 | poly[acrylamide-co-2-aminoethyl methacrylate hydrochloride (Weight ratio 50/50)* | 1.42 | 1 | Clear |
| 23 | poly[acrylamide-co-2-aminoethyl methacrylate hydrochloride (Weight ratio 50/50)* | 2.85 | 1 | Clear |
| 24 | poly[acrylamide-co-2-aminoethyl methacrylate hydrochloride (Weight ratio | 3.8 | 1 | Clear |

TABLE III-continued

| Ex. | Polymer | Concentrations (mg/mL) | Degree of Agglut. | Serum Integrity |
|---|---|---|---|---|
| 25 | poly[acrylamide-co-2-aminoethyl methacrylate hydrochloride (Weight ratio 50/50)* | 4.26 | 1 | Clear |
| 26 | poly(acrylamide-co-2-aminoethyl methacrylate hydrochloride) (Weight ratio 50/50) | 4.75 | 3 | Clear |
| 27 | poly(acrylamide-co-2-aminoethyl methacrylate hydrochloride) (Weight ratio 50/50) | 6.65 | 3 | Clear |
| 28 | poly(acrylamide-co-2-aminoethyl methacrylate hydrochloride) (Weight ratio 50/50) | 7.1 | 3 | Clear |
| 29 | poly(acrylamide-co-2-aminoethyl methacrylate hydrochloride) (Weight ratio 50/50) | 9.5 | 1 | Clear |
| 30 | poly(acrylamide-co-2-aminoethyl methacrylate hydrochloride) (Weight ratio 75/25) | 2.46 | 1 | Clear |
| 31 | poly(acrylamide-co-2-aminoethyl methacrylate hydrochloride) (Weight ratio 75/25) | 3.9 | 1 | Clear |
| 32 | poly(acrylamide-co-2-aminoethyl methacrylate hydrochloride) (Weight ratio 75/25) | 4.1 | 1 | Clear |
| Comp. Ex. 11 | poly(acrylamide-co-2-aminoethyl methacrylate hydrochloride) (Weight ratio 75/25)** | 0.82 | 0 | Clear |
| Comp. Ex. 12 | poly(acrylamide-co-2-aminoethyl methacrylate hydrochloride) (Weight ratio 75/25**) | 0.78 | 0 | Clear |
| Comp. Ex. 13 | poly(acrylamide-co-2-aminoethyl methacrylate hydrochloride) (Weight ratio 75/25**) | 2.34 | 0 | Clear |
| Comp. Ex. 14 | poly(acrylamide-co-2-aminoethyl methacrylate hydrochloride) (Weight ratio 75/25**) | 7.8 | 1 | Hemolysis |
| Comp. Ex. 15 | poly(acrylamide-co-2-aminoethyl methacrylate hydrochloride) (Weight ratio 75/25) | 15.6 | 1 | Hemolysis |
| Comp. Ex. 16 | poly(acrylamide-co-2-aminoethyl methacrylate hydrochloride (Weight ratio 75/25) | 23.4 | 1 | Hemolysis |
| Comp. Ex. 17 | poly[acrylamide-co-N-(3-aminopropyl)-methacrylamide hydrochloride] (Weight ratio 90/10)*** | 1.87 | 0 | Clear |
| Comp. Ex. 18 | poly[acrylamide-co-N-(3-aminopropyl)-methacrylamide hydrochloride] (Weight | 5.61 | 0 | Clear |

TABLE III-continued

| Ex. | Polymer | Concentrations (mg/mL) | Degree of Agglut. | Serum Integrity |
|---|---|---|---|---|
| Comp. Ex. 19 | ratio 90/10)*** poly[acrylamide-co-N-(3-aminopropyl)-methacrylamide hydrochloride] (Weight ratio 90/10)*** | 9.35 | 0 | Clear |

*The amide portion is considered to be inactive, so that the copolymer is characterizable as a primary amine, for Ex. 21-32 and the appropriate comparative examples.
**Apparently the reason why these differ in results over the results of Ex. 26-31, is the weight ratios of the monomers. That is, better results are obtained with less amount of the diluting acrylamide comonomer.
**Apparently the reason why these differ in results over the results of Ex. 26-31, is the weight ratios of the monomers. That is, better results are obtained with less amount of the acrylamide comonomer.
***Compare these with Ex. 15-17 above. Again, better results occur when lesser amounts of acrylamide are used as the comonomer.

Conclusions: A comparison of copolymers of the acrylamide comonomer indicates that, at least in the 75/25 weight ratio with the 2-aminoethyl methacrylate hydrochloride comonomer, a narrow concentration range occurs between having enough (at least 2.4 mg/mL) to produce an acceptable ("slight") agglutination, Ex. 30, and having so much (7.8 or more mg/mL) that the red cells hemolyze, Comp. Ex. 14, 15 and 16.

EXAMPLES 33-59

Secondary Amine Polymers

The secondary amine polymers tested were those of Table IV, which also gives the results:

TABLE IV

| Ex. | Polymer | Concentrations (mg/mL) | Degree of Agglut. | Serum Integrity |
|---|---|---|---|---|
| 33 | Poly[2-(N-methyl-amino)ethyl methacrylate HCl] | 0.25 | 1 | Clear |
| 34 | Poly[2-(N-methyl-amino)ethyl methacrylate HCl] | 0.75 | 1 | Clear |
| 35 | Poly[2-(N-methyl-amino)ethyl methacrylate HCl] | 1.0 | 1 | Clear |
| 36 | Poly[2-(N-methyl-amino)ethyl methacrylate HCl | 1.11 | 1 | Clear |
| 37 | Poly[2-N-methyl-amino)ethyl methacrylate HCl] | 1.25 | 1 | Clear |
| 38 | Poly[2-(N-methyl-amino)ethyl methacrylate HCl] | 1.67 | 1 | Clear |
| 39 | Poly[2-(N-methyl-amino)ethyl methacrylate HCl] | 2.22 | 3 | Clear |
| 40 | Poly[2-(N-methyl-amino)ethyl methacrylate HCl] | 2.78 | 3 | Clear |
| 41 | Poly[2-(N-methyl-amino)ethyl methacrylate HCl] | 2.97 | 1 | Clear |
| 42 | Poly[2-(N-methyl-amino)ethyl methacrylate HCl] | 3.0 | 1 | Clear |
| 43 | Poly[2-(N-methyl-amino)ethyl methacrylate HCl] | 3.33 | 1 | Clear |
| 44 | Poly[2-(N-methyl-amino)ethyl methacrylate HCl] | 5.0 | 1 | Clear |
| 45 | Poly[2-(N-methyl-amino)ethyl methacrylate HCl] | 5.55 | 1 | Clear |
| 46 | Poly[2-(N-methyl-amino)ethyl methacrylate HCl] | 8.91 | 1 | Clear |
| 47 | Poly[2-(N-methyl-amino)ethyl methacrylate HCl] | 14.85 | 1 | Clear |
| 48 | Poly[2-(N-methyl-amino)ethyl methacrylate HCl] | 17.82 | 1 | Clear |
| 49 | Poly[2-(N-methyl-amino)ethyl methacrylate HCl] | 20.8 | 1 | Clear |

TABLE IV-continued

| Ex. | Polymer | Concentrations (mg/mL) | Degree of Agglut. | Serum Integrity |
|---|---|---|---|---|
| Comp. Ex. 20 | Poly[2-(N-methyl-amino)ethyl methacrylate HCl] | 29.7 | 0 | Clear |
| Comp. Ex. 21 | Poly[2-(N-methyl-amino)ethyl methacrylate HCl] | 59.4 | 0 | Clear |
| Comp. Ex. 22 | Poly[2-(N-methyl-amino)ethyl methacrylate HCl] | 89.1 | 0 | Clear |
| 50 | Poly(acrylamide-co-2-(N-methylamino)ethyl methacrylate hydrochloride (weight ratio 60/40) | 0.85 | 1 | Clear |
| 51 | Poly(acrylamide-co-2-(N-methylamino)ethyl methacrylate hydrochloride (weight ratio 60/40) | 2.55 | 1 | Clear |
| 52 | Poly(acrylamide-co-2-(N-methylamino)ethyl methacrylate hydrochloride (weight ratio 60/40) | 4.25 | 1 | Clear |
| 53 | Poly(acrylamide-co-2-(N-methylamino)ethyl methacrylate hydrochloride (weight ratio 60/40) | 5.1 | 1 | Clear |
| 54 | Poly(acrylamide-co-2-(N-methylamino)ethyl methacrylate hydrochloride (weight ratio 60/40) | 5.95 | 1 | Clear |
| 55 | Poly(acrylamide-co-2-(N-methylamino)ethyl methacrylate hydrochloride (weight ratio 60/40) | 6.8 | 1 | Clear |
| 56 | Poly(acrylamide-co-2-(N-methylamino)ethyl methacrylate hydrochloride (weight ratio 60/40) | 7.65 | 1 | Clear |
| 57 | Poly(acrylamide-co-2-(N-methylamino)ethyl methacrylate hydrochloride (weight ratio 60/40) | 8.5 | 1 | Clear |
| 58 | Poly(acrylamide-co-N-isopropyl-N-vinylbenzylamine hydrochloride) (weight ratio 60/40) | 2.4 | 1 | Cloudy |
| 59 | Poly(acrylamide-co-N-isopropyl-N-vinylbenzylamine hydrochloride) (weight ratio 60/40) | 4.0 | 1 | Cloudy |
| Comp. Ex. 23 | Poly(acrylamide-co-N-isopropyl-N-vinylbenzylamine hydrochloride) (weight ratio 60/40) | 0.8 | 0 | Cloudy |
| Comp. Ex. 24 | Poly(N-isopropyl-N-vinylbenzylamine hydrochloride) | 0.23 | 0 | Hemolysis |
| Comp. Ex. 25 | Poly(N-isopropyl-N-vinylbenzylamine hydrochloride) | 0.31 | 0 | Hemolysis |
| Comp. Ex. 26 | Poly(N-isopropyl-N-vinylbenzylamine hydrochloride) | 0.69 | 0 | Hemolysis |
| Comp. Ex. 27 | Poly(N-isopropyl-N-vinylbenzylamine hydrochloride) | 0.93 | 0 | Hemolysis |
| Comp. Ex. 28 | Poly(N-isopropyl-N-vinylbenzylamine hydrochloride) | 1.0 | 0-1@ | Hemolysis |
| Comp. Ex. 29 | Poly(N-isopropyl-N-vinylbenzylamine hydrochloride) | 1.15 | 0@ | Hemolysis |
| Comp. Ex. 30 | Poly(N-isopropyl-N- | 1.55 | 0-1@ | Hemolysis |

TABLE IV-continued

| Ex. | Polymer | Concentrations (mg/mL) | Degree of Agglut. | Serum Integrity |
|---|---|---|---|---|
| | vinylbenzylamine hydrochloride) | | | |
| Comp. Ex. 31 | Poly(N-isopropyl-N-vinylbenzylamine hydrochloride) | 2.13 | 3 | Hemolysis |
| Comp. Ex. 32 | Poly(N-isopropyl-N-vinylbenzylamine hydrochloride) | 3.0 | 1 | Hemolysis |
| Comp. Ex. 33 | Poly(N-isopropyl-N-vinylbenzylamine hydrochloride) | 5.0 | 1 | Hemolysis |
| Comp. Ex. 34 | Poly(N-isopropyl-N-vinylbenzylamine hydrochloride) | 6.39 | 3 | Hemolysis |
| Comp. Ex. 35 | Poly(N-isopropyl-N-vinylbenzylamine hydrochloride) | 10.65 | 3 | Hemolysis |
| Comp. Ex. 36 | Poly(N-propyl-N-vinyl benzylamine HCl) | 0.22 | 0 | Hemolysis |
| Comp. Ex. 37 | Poly(N-propyl-N-vinyl benzylamine HCl) | 0.66 | 0 | Hemolysis |
| Comp. Ex. 38 | Poly(N-propyl-N-vinyl benzylamine HCl) | 1.1 | 0 | Hemolysis |

@ These three were difficult to evaluate as a borderline agglutination is slightly suggested in the results, but not enough to produce an outright "1" rating.

Conclusions: This data suggests that although a methyl group substituted onto the secondary amine nitrogen is satisfactory, a propyl (or larger) group may not be (e.g., Examples 58 and 59).

EXAMPLES 60-73

Tertiary Amine Polymers

Table V sets forth the polymers tested and their results.

TABLE V

| Ex. | Polymer | Concentrations (mg/mL) | Degree of Agglut. | Serum Integrity |
|---|---|---|---|---|
| 60 | Poly[N-(3-N,N-dimethylaminopropyl)methacrylamide] | 0.5 | 1 | Clear |
| 61 | Poly[N-(3-N,N-dimethylaminopropyl)methacrylamide] | 0.75 | 1 | Clear |
| 62 | Poly[N-(3-N,N-dimethylaminopropyl)methacrylamide] | 1.0 | 3 | Clear |
| 63 | Poly[N-(3-N,N-dimethylaminopropyl)methacrylamide] | 1.25 | 3 | Clear |
| 64 | Poly[N-(3-N,N-dimethylaminopropyl)methacrylamide] | 1.63 | 3 | Clear |
| 65 | Poly[N-(3-N,N-dimethylaminopropyl)methacrylamide] | 2.5 | 3 | Clear |
| 66 | Poly[N-(3-N,N-dimethylaminopropyl)methacrylamide] | 4.0 | 3 | Clear |
| 67 | Poly[N-(3-N,N-dimethylaminopropyl)methacrylamide] | 5.0 | 3 | Clear |
| 68 | Poly[N-(3-N,N-dimethylaminopropyl)methacrylamide] | 7.0 | 3 | Clear |
| 69 | Poly[N-(3-N,N-dimethylaminopropyl)methacrylamide] | 10 | 3 | Clear |
| 70 | Poly[N-(3-N,N-dimethylaminopropyl)methacrylamide] | 11.5 | 2 | Clear |
| 71 | Poly[N-(3-N,N-dimethylaminopropyl)methacrylamide] | 15.0 | 2 | Clear |
| 72 | Poly[N-(3-N,N-dimethylaminopropyl)methacrylamide] | 20 | 1 | Clear |
| 73 | Poly[N-(3-N,N-dimethylaminopropyl)methacrylamide] | 30 | 1 | Clear |

TABLE V-continued

| Ex. | Polymer | Concentrations (mg/mL) | Degree of Agglut. | Serum Integrity |
|---|---|---|---|---|
| Comp. Ex. 39 | Poly[N-(3-N,N-dimethylaminopropyl)methacrylamide] | 0.05 | 0 | Clear |
| Comp. Ex. 40 | Poly[N-(3-N,N-dimethylaminopropyl)methacrylamide] | 40 | 0 | Clear |
| Comp. Ex. 41 | Poly[acrylamide-co-N-(3-dimethylaminopropyl) methacrylamide] (weight ratio 60/40) | 0.88 | 0 | Clear |
| Comp. Ex. 42 | Poly[acrylamide-co-N-(3-dimethylaminopropyl) methacrylamide] (weight ratio 60/40) | 2.64 | 0 | Hemolysis |
| Comp. Ex. 43 | Poly[acrylamide-co-N-(3-dimethylaminopropyl) methacrylamide] (weight ratio 60/40) | 4.4 | 0 | Hemolysis |

The results of Table V indicate the importance in selecting an effective amount, since the results clearly peak at 1.0 to 10.0 mg/mL, with less than and more than that being less acceptable, although still useful. However, less than 0.5 mg/mL, and more than 30 mg/mL, is likely to be unacceptable. Ex. 62-69 also indicate why at least some tertiary amine polymers are considered to be outstanding, due to their best effectiveness over a wide concentration range at low concentrations (1 to 10 mg/mL).

EXAMPLES 74-79

Quaternary Amine Polymers

The following quaternary amine polymers were tested:

TABLE VII

| Ex. | Polymer | Concentrations (mg/mL) | Degree of Agglut. | Serum Integrity |
|---|---|---|---|---|
| 74 | Poly(N-cyclohexyl-N,N-dimethyl-N-vinylbenzylammonium chloride) | 2.0 | 1 | Clear |
| 75 | Poly(N-cyclohexyl-N,N-dimethyl-N-vinylbenzylammonium chloride) | 2.4 | 3 | Slightly Cloudy |
| 76 | Poly(N-cyclohexyl-N,N-dimethyl-N-vinylbenzylammonium chloride) | 4 | 3 | Cloudy |
| 77 | Poly(N-cyclohexyl-N,N-dimethyl-N-vinylbenzylammonium chloride) | 8 | 3 | Cloudy |
| 78 | Poly(N-cyclohexyl-N,N-dimethyl-N-vinylbenzylammonium chloride) | 8.3 | 3 | Cloudy |
| 79 | Poly(N-cyclohexyl-N,N-dimethyl-N-vinylbenzylammonium chloride) | 10.0 | 2 | Cloudy |
| Comp. Ex. 44 | Poly(N-cyclohexyl-N,N-dimethyl-N-vinylbenzylammonium chloride) | 0.8 | 0 | Clear |
| Comp. Ex. 45 | Poly(N-cyclohexyl-N,N-dimethyl-N-vinylbenzylammonium chloride) | 1.2 | 0 | Clear |
| Comp. Ex. 46 | Hexadimethrine bromide (Polybrene) [a comparative example because it is not a vinyl addition polymer or a poly(aminoacid)] | 0.5 | 0 | Clear |
| Comp. Ex. 47 | Hexadimethrine bromide (Polybrene) [a comparative example because it is not a vinyl addition polymer or a poly(aminoacid)] | 1.25* | 1 | Clear |
| Comp. Ex. 48 | Hexadimethrine bromide (Polybrene) [a com- | 9.0* | 1 | Clear |

TABLE VII-continued

| Ex. | Polymer | Concentrations (mg/mL) | Degree of Agglut. | Serum Integrity |
|---|---|---|---|---|
| | parative example because it is not a vinyl addition polymer or a poly(aminoacid)] | | | |
| Comp. Ex. 49 | Hexadimethrine bromide (Polybrene) [a comparative example because it is not a vinyl addition polymer or a poly(aminoacid)] | 10.0 | 0 | Clear |

*Also values of concentration in between 1.25 and 9.0 mg/mL were found to give the same results.

Conclusions: Ex. 75–79 demonstrate the usefulness of amine polymers that produce cloudy results.

The Comp. Ex. 46–49 are of particular interest, in that not only is Polybrene effective alone only at certain concentrations, but also it is not as effective as the most preferred polymers of this invention which produce a complete agglutination.

The invention has been described in detail with particular reference to certain preferred embodiments thereof, but it will be understood that variations and modifications can be effected within the spirit and scope of the invention.

What is claimed is:

1. Apparatus for separating and maintaining separated in a centrifuge, red cells from other constituents of whole blood, comprising
   a compartment constructed to receive whole blood for phase separation,
   and within said compartment, an effective amount of a coagulator accelerator agent for preventing said red cells from becoming resuspended when the compartment's contents are agitated, said agent having properties enabling lysing-free coagulation of blood cells and being effective when consisting essentially of a
   positively charged polymer, at neutral pH, that is either a polymerized amino acid having a weight average molecular weight of between about 35 k Daltons and about 500 k Daltons, determined by the LALLS light scattering technique, or a vinyl addition amine polymer having a PVP-eq. Mw of between about 40 PVP-eq. k Daltons and 6000 PVP-eq. k Daltons wherein the amine is a primary, secondary, tertiary or quaternary amine pendant from the polymer backbone and having a structure that is effective to coagulate without causing lysing of red blood cells.

2. Apparatus for separating and maintaining separated in a centrifuge, red cells from other constituents of whole blood, comprising
   a compartment constructed to receive whole blood for phase separation,
   and within said compartment, as a lysing-free coagulation agent effective when used alone, polylysine at a weight average molecular weight of between about 30 k Daltons and about 200 k Daltons determined by the LALLS light scattering technique.

3. Apparatus for separating and maintaining separated in a centrifuge, red cells from other constituents of whole blood, comprising
   a compartment constructed to receive whole blood for phase separation,
   and within said compartment, a coagulator acceleration agent having properties enabling lysing-free coagulation of blood cells and being effective when consisting essentially of a polymer having a PVP-eq. Mw of at least about 30 PVP-eq. k Daltons and recurring units with the structural formula

wherein $R_1$ is H or alkyl of 1–3 carbon atoms; $R_2$ is phenylenemethylene, $—CO_2R_3—$ or

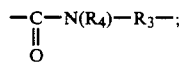

$R_3$ is alkylene of 1 to 6 carbon atoms; $R_4$ is alkyl of 1–4 carbon atoms or H; Q is a primary, secondary, tertiary or quaternary amine that does not lyse blood cells; the number of recurring units being that needed to create a PVP-eq. Mw of between about 40 PVP-eq. k Daltons and about 6000 PVP-eq. k Daltons.

4. Apparatus as defined in claim 3, wherein said polymer is selected from the group consisting of poly(2-aminoethyl methacrylate hydrochloride), poly[N-(3-aminopropyl)-methacrylamide], poly[N-(3-N,N-dimethylaminopropyl) methacrylamide], poly[2-(N-methylamino)ethylmethacrylate hydrochloride], poly[acrylamide-co-N-(3-aminopropyl)methacrylamide hydrochloride], poly(acrylamide-co-2-aminoethyl methacrylate hydrochloride), and poly(N-cyclohexyl-N,N-dimethyl-N-vinylbenzylammonium chloride).

5. Apparatus for separating and maintaining separated in a centrifuge, red cells from other constituents of whole blood, comprising
   a compartment constructed to receive whole blood for phase separation,
   and within said compartment, a coagulator acceleration agent having properties enabling lysing-free coagulation of blood cells and being effective when consisting essentially of a polymer having a PVP-eq. Mw of at least about 30 PVP-eq. k Daltons and recurring units with the structural formula

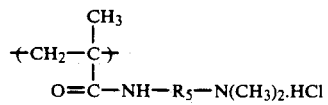

at a neutral pH, where $R_5$ is alkylene of from 1 to 3 carbon atoms.

6. Apparatus as defined in claim 5, wherein $R_5$ is $-(CH_2-)_3$.

7. A method of coagulating blood cells while centrifuging whole blood to separate out the serum, the method comprising the steps of
   (a) admixing in a container, a sample of whole blood and as a coagulator accelerator, an effective amount of an agent having properties enabling lysing-free coagulation of blood cells and being effective when consisting essentially of a positively charged polymer, at neutral pH, that is in the form of either a polymerized amino acid having a weight average molecular weight of between about 35 k and about 500 k Daltons determined by the LALLS light scattering technique, or a vinyl addition amine polymer having a PVP-eq. Mw of between about 40 PVP-eq. k Daltons and about 6000 PVP-eq. k Daltons wherein the amine is a primary, secondary, tertiary or quaternary amine pendant from the polymer backbone and having a structure that is effective to coagulate without causing lysing of red blood cells, said agent being effective without other coagulator accelerators present, and
   (b) spinning the container about a centrifuge axis at a speed sufficient to cause phase separation of the serum and blood cells, said quantity of acceleration being sufficient to cause said cells to permanently coagulate without lysing.

8. A method of coagulation as defined in claim 7, wherein said agent is selected from the group consisting of polylysine, poly(2-aminoethyl methacrylate hydrochloride), poly[N-(3-aminopropyl)methacrylamide], poly[N-(3-N,N-dimethylaminopropyl) methacrylamide], poly[2-(N-methylamino)ethylmethacrylate hydrochloride], poly[acrylamide-co-N-(3-aminopropyl)methacrylamide hydrochloride], poly(acrylamide-co-2-aminoethyl methacrylate hydrochloride), and poly(N-cyclohexyl-N,N-dimethyl-N-vinylbenzylammonium chloride).

9. A coagulated blood sample comprising serum, and adjacent thereto agglutinated blood cells intermixed with an effective amount of a coagulator accelerator agent for preventing said red cells from becoming resuspended when the compartment's contents are agitated, said agent
   having properties enabling lysing-free coagulation of blood cells and being effective when consisting essentially of a positively charged polymer, at neutral pH, that is either a polymerized amino acid having a weight average molecular weight of between about 35 k Daltons and about 500 k Daltons as determined by the LALLS light scattering technique, or a vinyl addition amine polymer having a PVP-eq. Mw of between about 40 PVP-eq. k Daltons and 6000 PVP-eq. k Daltons wherein the amine is a primary, secondary, tertiary or quaternary amine pendant from the polymer backbone and having a structure that is effective to coagulate without causing lysing of red blood cells.

10. A coagulated blood sample as defined in claim 9, wherein said agglutination is sufficiently complete as to resist resuspension of cells by inversion of the serum and agglutinated cells, and wherein said agent is selected from the group consisting of polylysine, poly(2-aminoethyl methacrylate hydrochloride), poly[N-(3-aminopropyl)methacrylamide], poly[N-(3-N,N-dimethylaminopropyl) methacrylamide], poly[2-(N-methylamino)ethyl methacrylate hydrochloride], poly[acrylamide-co-N-(3-aminopropyl)methacrylamide hydrochloride], poly(acrylamide-co-2-aminoethyl methacrylate hydrochloride), and poly(N-cyclohexyl-N,N-dimethyl-N-vinylbenzylammonium chloride).

* * * * *